United States Patent
Komatsu

[11] Patent Number: 5,811,306
[45] Date of Patent: Sep. 22, 1998

[54] LIQUID SPOTTING METHOD

[75] Inventor: Akihiro Komatsu, Kanagawa-ken, Japan

[73] Assignee: Fuji Photo Film Co., Ltd., Kanagawa-Ken, Japan

[21] Appl. No.: 707,515

[22] Filed: Sep. 4, 1996

[30] Foreign Application Priority Data

Sep. 4, 1995 [JP] Japan .................................. 7-226557
Sep. 25, 1995 [JP] Japan .................................. 7-246062

[51] Int. Cl.$^6$ .................................................. G01N 35/10
[52] U.S. Cl. ........................... 436/54; 436/43; 436/46; 436/50; 436/180; 422/63; 422/81; 422/100; 73/864.11; 73/864.22; 73/864.24
[58] Field of Search .................... 436/43, 46, 50, 436/54, 174, 180; 422/63, 64, 66, 67, 81, 100; 73/864.24, 864.25, 864.11; 141/130, 351, 352, 251, 258, 260, 263

[56] References Cited

U.S. PATENT DOCUMENTS

| | | |
|---|---|---|
| 4,340,390 | 7/1982 | Collins et al. ........................... 23/230 |
| 4,452,899 | 6/1984 | Alston ..................................... 436/46 |
| 4,675,301 | 6/1987 | Charneski et al. ..................... 436/180 |
| 4,794,085 | 12/1988 | Jessop et al. ............................ 436/54 |
| 4,971,763 | 11/1990 | Columbus .............................. 422/100 |
| 5,133,392 | 7/1992 | Hamann .................................... 141/1 |
| 5,143,849 | 9/1992 | Barry et al. ............................. 436/50 |
| 5,607,861 | 3/1997 | Komatsu et al. ........................ 436/50 |

*Primary Examiner*—Long V. Le
*Attorney, Agent, or Firm*—Sughrue, Mion, Zinn, Macpeak & Seas, PLLC

[57] ABSTRACT

A method of continuously spotting a liquid onto a predetermined number of members to be spotted with the liquid includes the steps of mounting a disposable spotting tip on a suction nozzle, sucking the liquid in the spotting tip in a predetermined amount larger than the predetermined number times the amount for one spotting and discharging the liquid onto the members in sequence by the amount for one spotting by introducing a predetermined discharge pressure into the spotting tip. A signal related to the vapor pressure in atmosphere is obtained and the discharge pressure is corrected according to the change in the vapor pressure inside the spotting tip after the liquid is sucked in the spotting tip so that the same amount of the liquid is discharged onto all the members.

9 Claims, 12 Drawing Sheets

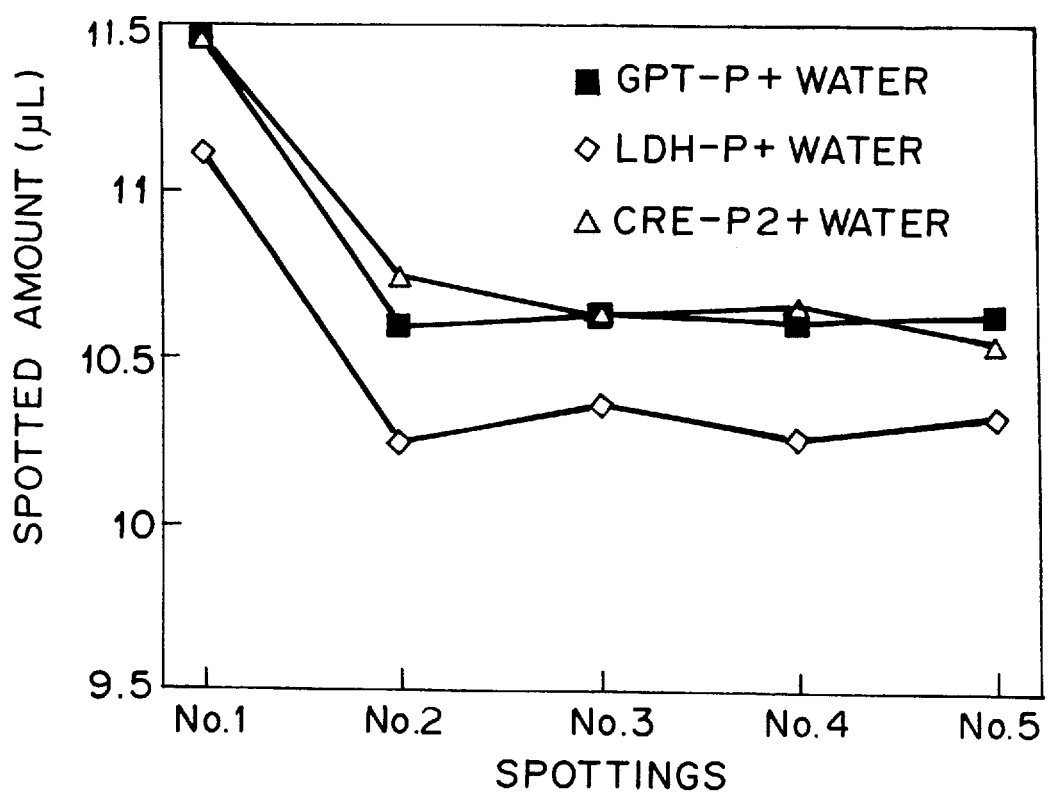

LIQUID SPOTTING METHOD

BACKGROUND OF THE INVENTION

1. Field of the Invention

This invention relates to a liquid spotting method and a liquid spotting device for spotting a sample liquid such as blood or urine, a diluent liquid, a reference liquid or the like onto a member to be spotted with the liquid such as a dry chemical analysis element, a dilution cup or the like, and more particularly to such a liquid spotting method and a liquid spotting device in which a liquid held in a disposable spotting tip is continuously spotted onto a member in a constant amount.

2. Description of the Related Art

There has been put into practice a dry ("dry-to-the-touch") chemical analysis element with which a specific chemical component or a solid component contained in a sample liquid can be quantitatively analyzed by only spotting a droplet of the sample liquid onto the element. See, for instance, U.S. Pat. Nos. 3,992,158 and 4,292,272. When such a dry chemical analysis element is used, the sample liquid can be analyzed more easily and more quickly than when the conventional wet analysis method is used, and accordingly the dry chemical analysis element is very convenient for medical facilities, laboratories and the like where lots of sample liquids have to be analyzed.

When quantitatively analyzing the chemical components or the like contained in a sample liquid using such a dry chemical analysis element, a droplet of the sample liquid is spotted onto the element and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the element is projected onto the element and the optical density of the element is measured. Then the concentration of the component to be analyzed is determined on the basis of the optical density using a calibration curve which represents the relation between the concentration of the biochemical component and the optical density. Thereafter the chemical analysis element is taken out from the incubator and discarded in a discarding box.

The chemical analysis element generally comprises a chemical analysis film in the form of a chip having a reagent layer formed on a support sheet of organic polymer or the like. The chemical analysis film chip is sometimes used as it is, and sometimes used in the form of a slide comprising such a chemical analysis film chip and a frame of organic polymer or the like which supports flat the film chip. In such a chemical analysis element, it is important that the sample liquid is spotted onto the element accurately in a predetermined amount in order to ensure accuracy of the measurement.

Further when a sample liquid is diluted to a predetermined concentration, the sample liquid and diluent must be spotted in a dilution cup accurately in predetermined amounts.

Further there has been known a dry electrolyte analysis slide for measuring the concentration of an electrolyte in a sample liquid. The electrolyte analysis slide has a pair of electrodes. When measuring the concentration of an electrolyte in a sample liquid using the electrolyte analysis slide, a sample liquid and a reference liquid are spotted onto the slide and the concentration of the electrolyte is determined on the basis of a potential difference. Also in this case, the sample liquid and the reference liquid must be spotted accurately in predetermined amounts.

As a way of spotting a liquid such as a sample liquid, diluent liquid, reference liquid or the like onto a member such as a dry chemical analysis element, a dilution cup or the like, there has been known a method in which the liquid is once sucked in a suction nozzle and is discharged on the member with the suction nozzle washed every time the kind of the liquid is changed. However this method is disadvantageous in that when the liquid remains on the nozzle, contamination occurs to deteriorate accuracy of measurement and that the nozzle washing process deteriorates the time efficiency of the system. In order to overcome such a problem, there has been put into practice a method in which a disposable spotting tip is mounted on said suction nozzle so that the liquid is sucked in the spotting tip and the spotting tip is changed every time the kind of the liquid is changed. See U.S. Pat. No. 4,340,390 and the like.

When spotting is effected by sucking liquid in an amount corresponding to one spotting in the spotting tip and discharging the whole liquid in the spotting tip onto a member to be spotted with the liquid, the liquid cannot be spotted accurately in a predetermined amount. That is, a part of the liquid is apt to remain on the end of the spotting tip under a surface tension and an attempt to entirely spot the liquid held in the spotting tip results in forming bubbles in the spotted liquid.

It may be expected that the liquid can be spotted more accurately in a predetermined amount when the liquid is sucked in the spotting tip in an amount larger than that for one spotting so that only a part of the liquid held in the spotting tip is discharged. Further when a liquid is to be spotted onto a plurality of members to be spotted with the liquid, the steps of sucking the liquid in the spotting tip in an amount larger than that for one spotting and discharging a part of the liquid held in the spotting tip onto the member are repeated for each of the members or the liquid is sucked in the spotting tip in an amount larger than the number of spottings times the amount for one spotting and discharged onto the members in sequence by the amount for one spotting.

In the method disclosed in the above identified United States patent, the suction system is vented to atmosphere each time the liquid is sucked into the spotting tip to return the pressure inside the spotting tip to atmospheric pressure so that the liquid level in the spotting tip is lowered to a position where the liquid in the spotting tip balances with surface tension on the inner surface of the spotting tip and then the liquid in the spotting tip is discharged.

However, when the liquid is sucked in the spotting tip in an amount larger than the number of spottings times the amount for one spotting and discharged onto the members in sequence by the amount for one spotting, the amount of the liquid actually spotted fluctuates from one spotting to another.

That is, as shown in FIG. 11 where a result of an experiment is shown, the amount of the liquid spotted in the first spotting is larger than that spotted in any other spotting. In this experiment, a new spotting tip was mounted on the suction nozzle and water was sucked in the spotting tip in an amount larger than that for a predetermined number of spottings at one time. Then the water was discharged onto the predetermined number of chemical analysis elements at intervals of 9 seconds by introducing the same discharge pressure into the spotting tip for each spotting so that a target amount of (e.g., 10 µL) water is spotted in each spotting. Three kinds of chemical analysis elements were used and the amount of spotted water differed by the kind of the chemical analysis element. However, irrespective of the kind of the chemical analysis element, the actual amount of water spotted in the first spotting was larger than that spotted in any other spotting by about 0.7 to 0.9 µL.

One of the three kinds of chemical analysis element was for measuring glutamic-pyruvic transaminase (GPT-P), another for measuring lactate dehyrogenase (LDH-P) and the other for measuring creatinine. The experiment was carried out in an atmosphere at a temperature of 32° C. and a relative humidity of 30%.

It has been found that fluctuation in the vapor pressure in the spotting tip causes the actual amount of water spotted in the first spotting to be larger than that spotted in any other spotting. That is, when water is sucked in a new spotting tip, which is dry, the space in the spotting tip above the water is at a vapor pressure at the temperature and the humidity of the atmosphere as shown in FIG. 12A. (In this state, after water is sucked in the spotting tip, air is sucked in the spotting tip to raise the water level L.) However as the time lapses, the water in the spotting tip evaporates and the pressure inside the spotting tip rises to lower the water level L as shown in FIG. 12B. Accordingly when a predetermined discharge pressure is introduced into the spotting tip to increase the pressure inside the spotting tip to discharge the water as shown in FIG. 12C, the pressure inside the spotting tip is excessively increased by a value corresponding to increase in the vapor pressure and accordingly an excessive amount of water is discharged in the first spotting. After the first spotting, the vapor pressure inside the spotting tip is saturated and does not fluctuate, whereby the amount of spotted water is stabilized.

The reason why the amount of spotted water differs by the kind of chemical analysis element may be the difference in wetting due to difference in the reagent layer between the chemical analysis elements.

When the inside of the spotting tip is vent to atmosphere for each spotting as in the above identified United States patent, generation of difference in amount of spotted liquid due to influence of the vapor pressure may be prevented. However since the position where the liquid in the spotting tip balances with surface tension on the inner surface of the spotting tip varies according to the wetting (water repellency) of the inner surface of the spotting tip, the viscosity of the liquid and the like, the amount of spotted liquid can fluctuate. Further the method is disadvantageous in that an off-off valve is required in the suction system, which complicates the system.

Thus in continuously spotting liquid onto a plurality of members to be spotted with the liquid using a disposable spotting tip, there has been a problem that there is a difference in the amount of liquid actually spotted onto the member for a given discharge pressure between a spotting before the vapor pressure is saturated and a spotting after the vapor pressure is saturated.

Further as the method of spotting a sample liquid onto a dry chemical analysis element, there has been known a method in which after the sample liquid is sucked into a disposable spotting tip, a droplet is formed on the lower end of the spotting tip, the spotting tip is moved downward toward the chemical analysis element until the droplet is brought into contact with the chemical analysis element and the spotting tip is stopped to permit the droplet to spread over the upper surface of the chemical analysis element.

Further as disclosed in U.S. Pat. No. 4,340,390, there has been known a method in which the spotting tip is lowered to a position where the lower end thereof is at a predetermined distance from the upper surface of the chemical analysis element and then the sample liquid in the spotting tip is discharged at a predetermined rate.

With either of the methods, even a slight coagulation of the droplet on the lower end of the spotting tip can cause error in the amount of spotted sample liquid when a very small amount (e.g., a few µL) of sample liquid is to be spotted.

In order to suppress generation of the error due to coagulation of the droplet, it has been proposed to suck air into the spotting tip after sucking the sample liquid, thereby raising the lower surface of the sample liquid in the spotting tip above the lower end of the spotting tip as disclosed in Japanese Unexamined Patent Publication 1(1989)-184464. However it has been found that this method is disadvantageous in that a bubble is formed in the lower surface of the sample liquid in the spotting tip, which can cause error in the amount of spotted sample liquid.

That is, generally the suction nozzle on which the spotting tip is mounted is supported by an arm member and the arm member is moved up and down and in horizontal directions in order to spot the sample liquid held in the spotting tip onto a chemical analysis element. It has been found that during such motions of the arm member, the spotting tip 301 is vibrated and the vibration of the spotting tip 301 generates a bubble 305 as shown in FIG. 13B in the lower surface of the sample liquid 304 which has been sucked inside the spotting tip 301 so that the lower surface thereof is positioned higher than the lower end of the spotting tip 301 as shown in FIG. 13A.

This inventor has recognized that the bubble 305 is formed in the following manner. That is, the spotting tip for spotting a very small amount of liquid should be very small in inner diameter. However when the entire spotting tip is thin, the spotting tip becomes apt to deform and apt to swing in the lateral direction to a large extent by mechanical vibrations, which prevents an accurate spotting action. Accordingly it is preferred that the spotting tip be thick as a whole to increase strength in deform with the lower end portion made very thin to enable spotting of a very small amount of liquid. Thus the spotting tip for spotting a very small amount of liquid naturally should comprise an upper portion 301a (FIG. 13B) having a larger diameter, a lower portion 301b having a smaller diameter and a tapered portion 301c connecting the upper and lower portions 301a and 301b. That is, the inner diameter of the spotting tip discontinuously increases toward the direction away from the sucking port of the spotting tip in the range where the sucked liquid occupies. With the spotting tip 301 of such a shape, when the sample liquid 304 is sucked into the spotting tip 301 to a position where the lower surface of the sample liquid 304 is higher than the boundary 301d between the lower portion 301b and the tapered portion 301c, thin film of the sample liquid 304 formed on the inner surface of the spotting tip 301 when the sample liquid 304 is sucked upward frequently comes to extend across the inner space of the spotting tip 301 at the lower end of the thin film due to vibrations, thereby forming a bubble about the tapered portion 301c.

Thus there has been a demand for a liquid spotting method which can spot a very small amount of liquid with a spotting tip having a tapered portion without formation of a bubble in the lower portion of the liquid sucked into the spotting tip above the lower end thereof.

SUMMARY OF THE INVENTION

In view of the foregoing observations and description, the primary object of the present invention is to provide a liquid spotting method which can spot liquid onto a member to be spotted with the liquid accurately in a predetermined amount with a simple mechanism without use of an on-off valve or the like.

Another object of the present invention is to provide a liquid spotting device for carrying out the method.

Still another object of the present invention is to provide a liquid spotting method which can spot a very small amount of liquid with a spotting tip having a tapered portion without formation of a bubble in the lower portion of the liquid sucked into the spotting tip above the lower end thereof.

In accordance with one aspect of the present invention, there is provided a method of continuously spotting a liquid onto a predetermined number of members to be spotted with the liquid comprising the steps of mounting a disposable spotting tip on a suction nozzle, sucking the liquid in the spotting tip in a predetermined amount larger than the predetermined number times the amount for one spotting and discharging the liquid onto the members in sequence by the amount for one spotting by introducing a predetermined discharge pressure into the spotting tip, wherein the improvement comprises the steps of obtaining a signal related to the vapor pressure in atmosphere and correcting the discharge pressure according to the change in the vapor pressure inside the spotting tip after the liquid is sucked in the spotting tip so that the same amount of the liquid is discharged onto all the members.

The saturated vapor pressure inside the spotting tip increases as the atmospheric temperature increases and the difference from the saturated vapor pressure increases as the atmospheric humidity decreases. The amount of correction is determined according to such characteristics. However in order to simplify the correction according to the atmospheric condition, the amount of correction may be determined according to one of the temperature and the humidity.

Specifically the correction is made so that the discharge pressure at the first spotting becomes lower than that at the second spotting or the correction is made for the spottings which are made before the vapor pressure in the spotting tip is saturated.

In accordance with another aspect of the present invention, there is provided a liquid spotting device comprising a liquid sucking/discharging means which sucks a predetermined amount of liquid in a spotting tip mounted on a suction nozzle and discharges the liquid onto a member to be spotted with the liquid by introducing a predetermined discharge pressure into the spotting tip, a detecting means which detects a signal related to the vapor pressure in atmosphere and a correcting means which calculates a correction amount for the discharge pressure according to a preset correction characteristic on the basis of the signal detected by the detecting means and outputs a correction signal to the liquid sucking/discharging means.

By thus correcting the discharge pressure, lowering of the liquid level due to increase in the vapor pressure inside the spotting tip can be compensated for and the liquid can be spotted accurately in a predetermined amount without affected by wetting and the like of the inner surface of the spotting tip. Further since an additional mechanism such as an on-off valve is not required, cause of failure is not increased. Further, the present invention can be realized only by adding a correcting means to the original discharge amount control mechanism in the conventional liquid spotting device, which is advantageous from the viewpoint of cost.

In accordance with still another aspect of the present invention, there is provided a liquid spotting method comprising the steps of sucking liquid into a spotting tip and then sucking air into the spotting tip to suppress coagulation of the liquid, wherein the improvement comprises that air is sucked into the spotting tip to a predetermined level where the lower surface of the liquid held in the spotting tip is positioned between an upper limit above which a bubble can be formed in the lower portion of the liquid held in the spotting tip when the spotting tip vibrates and a lower limit below which the liquid held in the spotting tip can coagulate from the lower surface thereof.

In this specification, the expression "air is sucked into the spotting tip to a predetermined level" should be broadly interpreted to include a case where air is once sucked into the spotting tip beyond the predetermined level and then discharged to the predetermined level before the arm member begins its action and vibration begins to be transmitted to the spotting tip. That is, air may be once sucked to a level where the lower surface of the liquid held in the spotting tip is positioned above the upper limit and then discharged to a level where the lower surface of the liquid held in the spotting tip is positioned between the upper limit and the lower limit.

The upper limit is a critical position above which a bubble can be formed in the lower portion of the liquid held in the spotting tip by vibration and depends upon the inner diameter of the spotting tip at the boundary between the lower portion (smaller diameter portion) and the tapered portion, the angle of the tapered portion, the material of the spotting tip, the kind of the liquid, the viscosity of the liquid, the magnitude of vibration transmitted to the spotting tip and the like. The upper limit can be empirically determined with ease when the spotting tip used and the conditions of use are determined.

It has been found that the upper limit is generally exists near a position where the center of the lower surface of the liquid held in the spotting tip is on a level higher than the boundary between the smaller diameter portion and the tapered portion by the inner diameter of the spotting tip at the boundary. Practically when the upper limit is set at this position, a satisfactory result can be frequently obtained.

The lower limit is a critical position below which the liquid held in the spotting tip can coagulate to such an extent that can cause an error in the amount of spotted liquid which cannot be neglected. The lower limit depends upon the accuracy requirement for the amount of spotted liquid, the inner diameter of the spotting tip, the shape of the lower end portion of the spotting tip, the kind of the liquid to be spotted and the like, and can be empirically determined with ease when these conditions are determined.

It has been found that the lower limit generally exists near a position where the center of the lower surface of the liquid held in the spotting tip is on a level higher than the lower end of the spotting tip by the inner diameter of the spotting tip at the lower end. Practically when the lower limit is set at this position, a satisfactory result can be frequently obtained.

It is preferred that the inner diameter of the spotting tip at the boundary between the small diameter portion and the tapered portion be not smaller than 0.5 mm and not larger than 2 mm.

BRIEF DESCRIPTION OF THE DRAWINGS

FIG. 11 is a graph showing the change in the amount of the liquid actually spotted with the number of spottings when a plurality of members are continuously spotted with the liquid.

DESCRIPTION OF THE PREFERRED EMBODIMENT

Figure 2:
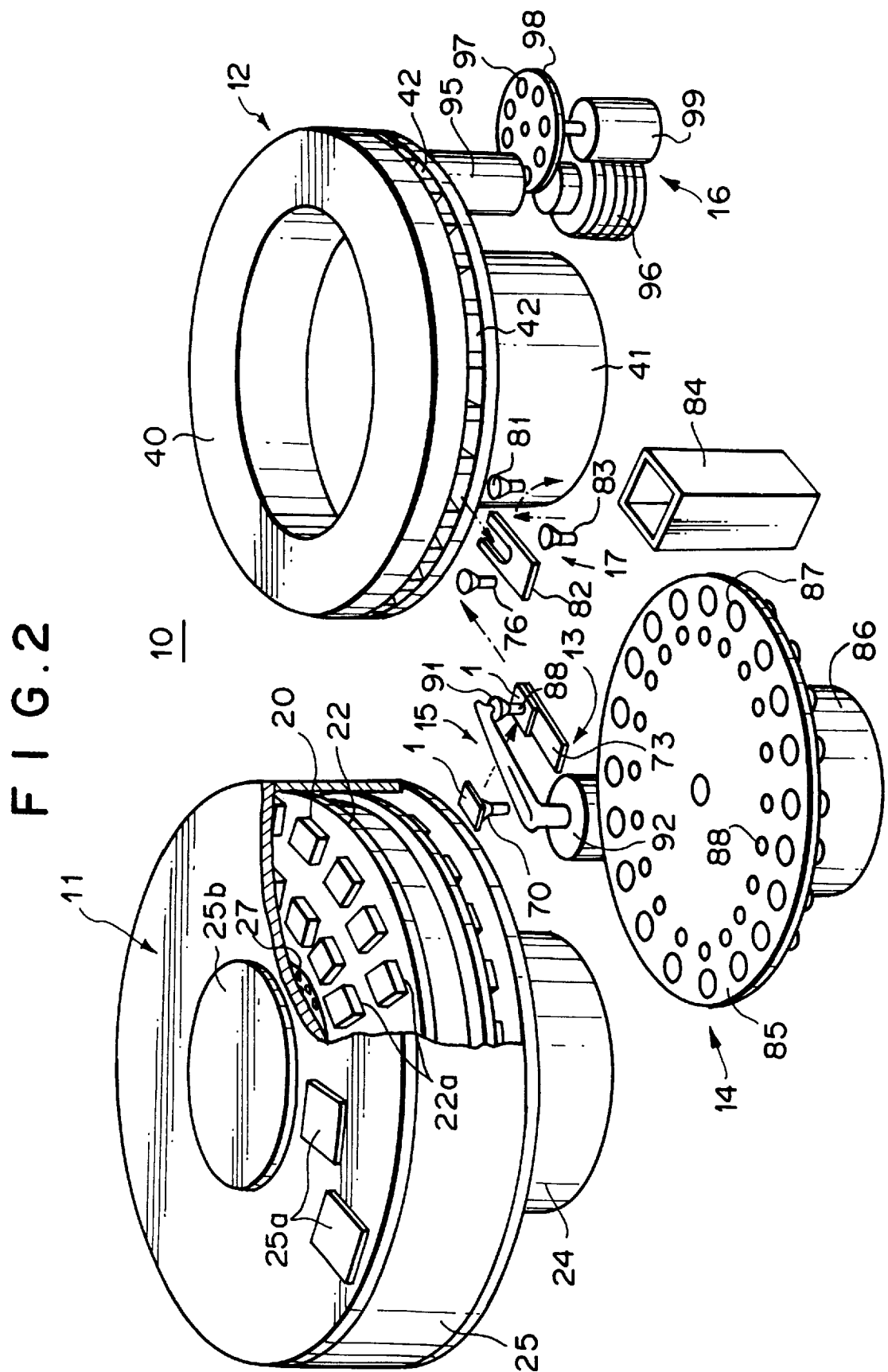
FIG. 2 is a schematic perspective view showing a biochemical analysis apparatus provided with the liquid spotting device shown in FIG. 1.

FIG. 2 shows a biochemical analysis apparatus 10 provided with a liquid spotting device in accordance with an embodiment of the present invention. As shown in FIG. 2, the biochemical analysis apparatus 10 comprises a film supplier 11 in which a plurality of virgin dry frameless chemical analysis films 1 (which are rectangular or square in shape) are stored, an incubator 12 which is disposed beside the film supplier 11 and incubates the frameless chemical analysis films 1 spotted with sample liquids for a predetermined time at a constant temperature, a film transfer means 13 which transfers the frameless chemical analysis films 1 from the film supplier 11 to the incubator 12, a sample liquid supplier 14 in which a plurality of sample liquids such as serum, urine or the like are stored, a spotting device 15 which spots one of the sample liquids in the sample liquid supplier 14 on the frameless chemical analysis film 1 on the way to the incubator 12, and a light measuring system 16 disposed below the incubator 12.

Figure 3:
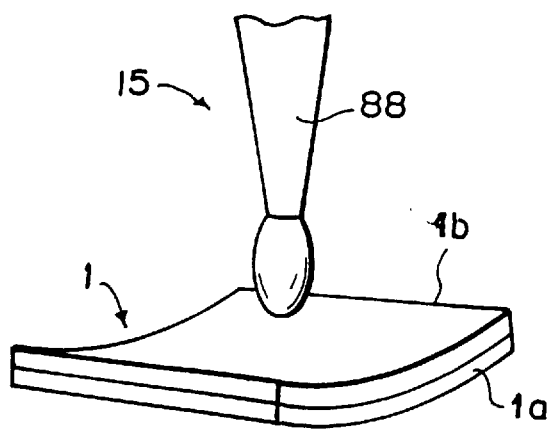
FIG. 3 is a perspective view showing spotting of the sample liquid onto the frameless chemical analysis film.

As shown in FIG. 3, the frameless chemical analysis film 1 comprises a light-transmissive support sheet 1a formed of plastic film such as polyethylene terephthalate (PET) and a reagent layer 1b including a spreading layer formed on the support sheet 1a. If desired a protective layer (not shown) formed of a material resistant to rubbing such as fabric may be formed over the reagent layer, and such a protective layer may double as the spreading layer.

In a dry state, the film 1 is warped (curled or curved) toward the reagent layer 1b, the degree of warp depending upon the kind of the reagent layer 1b and the dryness of the film 1. The reagent layer 1b of the frameless chemical analysis film 1 contains therein reagent (chemical analysis reagent or immunoassay reagent) which makes a coloring reaction (coloring substance forming reaction) with a particular component in the sample liquid spotted from a nozzle tip 88 of the spotting device 15 (to be described later) after incubation for a predetermined time. A plurality of kinds of frameless chemical analysis films 1 having reagent layers 1b for different analytes (chemical component or solid component to be analyzed) are prepared.

Figure 4:
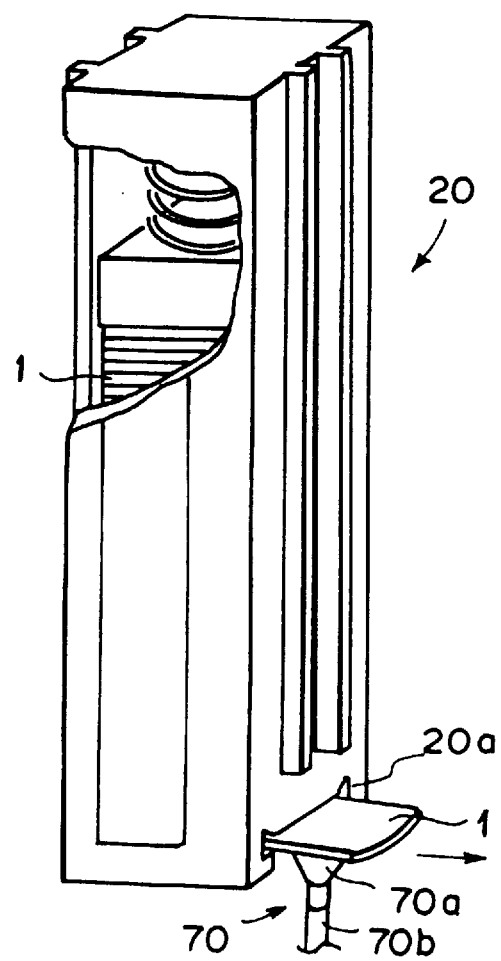
FIG. 4 is a perspective view showing the manner of taking out the frameless chemical analysis film from the cartridge.

The chemical analysis films 1 are stacked in cartridges 20 shown in FIG. 4 for the respective analytes with the support sheets 1a facing downward. A plurality of the cartridges 20 are respectively loaded in a plurality of cartridge holding portions 22a formed in a disk-like support member 22 in the film supplier 11 in inner and outer circles. The support member 22 is supported for rotation on a base 24 and is rotated by a supplier motor (not shown) to bring a desired cartridge 20 to a film take-out position where the film transfer means 13 takes out the film 1 in the cartridge 20.

The film supplier 11 is provided with a cover 25 which tightly encloses the inner space of the film supplier 11. The cover 25 is provided with a pair of openings 25a provided with lids and the cartridges 20 are taken out and inserted into the cartridge holding portions through the openings 25a. An dehumidifying agent holding portion 27 is formed in the support member 22 at the center thereof and dehumidifying agent (desiccant) is loaded in the dehumidifying agent holding portion through an opening 25b formed in the cover 25. The opening 25b is provided with a lid. Thus the inner space of the film supplier 11 is kept dry. A shutter (not shown) is provided in the lower surface of the film supplier 11 in the film take-out position. The shutter is opened when the film 1 is taken out from the cartridge 20 and a film take-out member 70 of the film transfer means 13 takes out the lowermost film 1 in the cartridge 20 through the shutter.

The incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The chemical analysis films 1 are incubated in the cells 42.

The film transfer means 13 for transferring the film 1 from the film supplier 11 to the incubator 12 comprises said film take-out member 70 for taking out the film 1 from the cartridge 20, a horseshoe-like delivery member 73 which receives the film 1 held on the suction pad 70a from below the film 1 with the reagent layer 1b facing upward and inserts the film 1 into the cell 42 in the incubator 12, and a suction member 76 which moves in and out the cell 42 from below the cell 42 and receives the film 1 held by the delivery member 73 inside the cell 42.

As shown in FIG. 4, the film take-out member 70 has a suction pad 70a which is directed upward and holds the lower surface of the support sheet 1a of the frameless chemical analysis film 1 under a suction force. The suction pad 70a is supported by a conveying base portion 70b and a suction hose (not shown) connects the suction pad 70a to a suction pump (not shown). The conveying base portion 70b is moved back and forth and up and down by a drive mechanism (not shown) to move the suction pad 70a back and forth and up and down.

The suction pad 70a is moved upward and into the cartridge 20 through the opening in the bottom of the cartridge 20 and holds the support sheet 1a of the lowermost frameless chemical analysis film 1 under the suction force. Then the suction pad 70a is slightly moved downward holding the film 1 and then moved horizontally toward the center of the support member 22 to take out the film 1 through a film take-out opening 20a in the side wall of the cartridge 20. Thereafter the suction pad 70a is moved downward outside the film supplier 11 through the opening in the cover 25 and moved away from the support member 22 to convey the film 1 to a spotting position.

Figure 5:
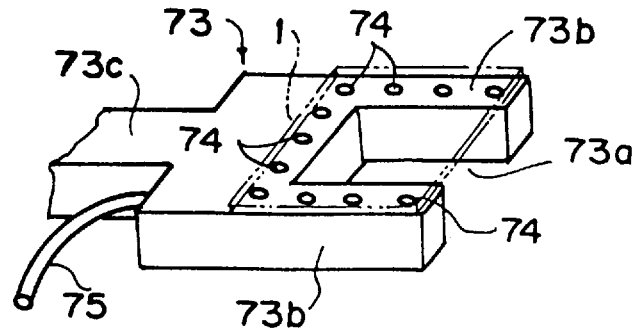
FIG. 5 is a fragmentary perspective view of the film delivery member.

As shown in FIG. 5, the delivery member 73 is like a horseshoe in shape and has a flat upper surface. That is, the delivery member 73 is bifurcated in the front end portion to form of a pair of arm portions 73b extending on opposite sides of a cutaway portion 73a, and a plurality of suction holes 74 are formed to surround the cutaway portion 73a and to open in the upper surface of the delivery member 73. The suction holes 74 are connected to a suction pump (not shown) through vacuum tube 75. The base portion 73c of the delivery member 73 is connected to a drive mechanism (not shown) to be moved from the spotting position toward the center of the incubator 12 and inserted into the cell 42 through the side opening of the incubator 12.

Figure 6A:
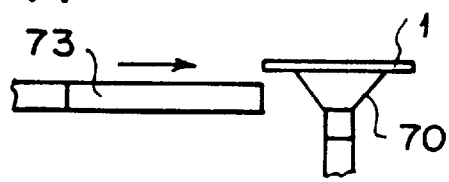
FIGS. 6A to 6C are views for illustrating transfer of the frameless chemical analysis film from the suction pad to the film delivery member.
Figure 6B:
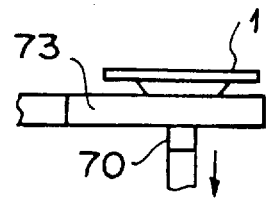
Figure 6C:
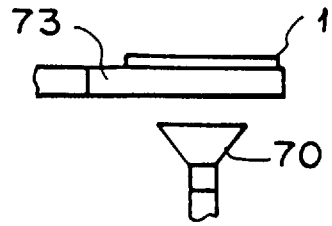

When the delivery member 73 receives the frameless chemical analysis film 1 from the suction pad 70a, the delivery member 73 is moved toward the suction pad 70a holding the film 1 as shown in FIG. 6A, and is stopped in a position where the suction pad 70a is in the cutaway portion 73a of the delivery member 73 with the film 1 positioned above the cutaway portion 73a as shown in FIG. 6B. Then the suction pad 70a is moved downward below the delivery member 73 leaving the film 1 on the delivery member 73 as shown in FIG. 6C. The film 1 left on the delivery member 73 is held thereon under the suction force provided through the suction holes 74. Thus the film 1 can be transferred to the delivery member 73 accurately in place, whereby a predetermined amount of the sample liquid can be accurately spotted by the spotting device 15 onto the center of the reagent layer 1b held by the delivery member 73.

The sample liquid supplier 14 comprises a turn table 85 which is rotated by a drive mechanism 86 as shown in FIG. 2. The turn table 85 holds a plurality of sample containers 87 filled with sample liquids which are arranged along the circumferential edge of the turn table 85 and is rotated to bring the sample containers 87 to a sample liquid supplying position one by one. A plurality of nozzle tips 88 which are mounted on a suction nozzle 91 to be described later are held on the turn table 85 inside the sample containers 87.

The spotting device 15 for spotting the sample liquid onto the film 1 comprises a suction nozzle 91 which sucks and discharges the sample liquid, and a spotting tip 88 like a pipette is demountably mounted on the nozzle 91. The nozzle 91 is moved up and down and rotated by a drive mechanism 92. That is, the nozzle 91 sucks the sample liquid from the sample liquid supplier 14 into spotting tip 88, is moved to the film 1 held by the delivery member 73, and then spots the sample liquid onto the film 1. The spotting tip 88 is changed every time the sample liquid is changed.

Figure 1:
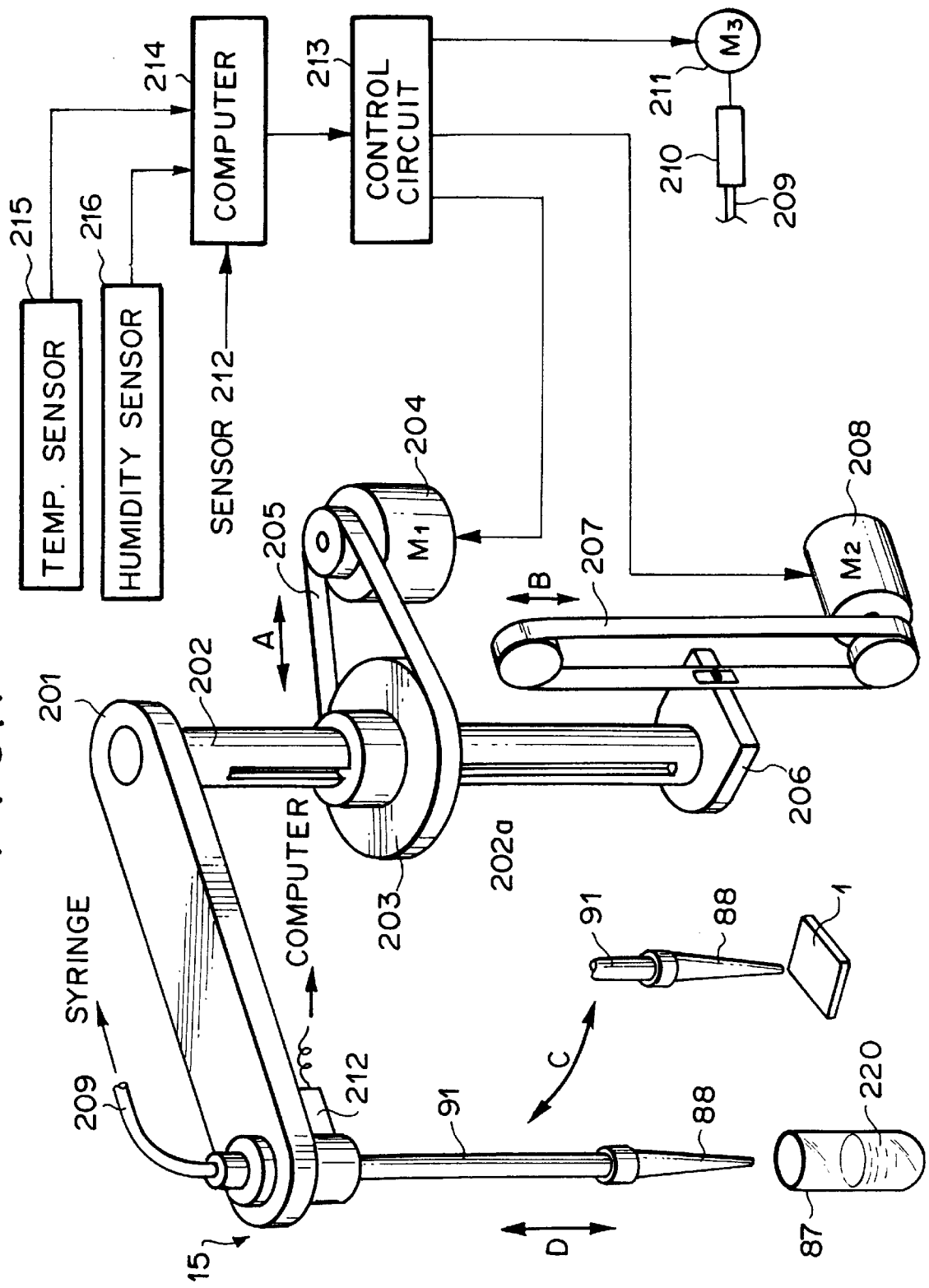
FIG. 1 is a schematic view showing a liquid spotting device in accordance with an embodiment of the present invention.

As shown in FIG. 1, the spotting device 15 comprises a sampling arm 201 supported on a vertical spline shaft 202 at one end thereof to extend horizontally from the top of the spline shaft 202. The suction nozzle 91 is supported for up-and-down movement on the other end of the sampling arm 201. The spline shaft 202 has a keyway 202a formed on the side surface thereof to extend in the longitudinal direction of the spline shaft 202. A pulley 203 having a larger diameter portion and a smaller diameter portion is fitted on the spline shaft 202 with its key in engagement with the keyway 202a of the spline shaft 202 so that the spline shaft 202 is rotated together with the pulley 203 while permitting the pulley 203 to slide relative to the spline shaft 202 in the longitudinal direction thereof. A belt 205 is passed around the pulley 203 and the output shaft of a first motor 204 and the pulley 203 is rotated back and forth as shown by arrow A driven by the first motor 204. A collar 206 is fixed to the lower end of the spline shaft 202 and a belt 207 is fixed to the collar 206. The belt 207 is driven back and forth by a second motor 208 as shown by arrow B to move up and down the spline shaft 202.

The spotting device 15 is provided with a sample liquid sucking/discharging means which adjusts the pressure inside the suction nozzle 91 and the spotting tip 88 to suck the sample liquid into the spotting tip 88 and to discharge the sample liquid from the tip 88. The sample liquid sucking/discharging means comprises a air hose 209, a syringe 210, a third motor 211 and a nozzle position sensor 212 which detects the up-and-down movement of the suction nozzle 91.

The syringe 210 has a piston which is moved back and forth to generate a negative pressure and a positive pressure inside the syringe 210 in response to regular and reverse rotation of the third motor 211. The negative or positive pressure generated in the syringe 210 is introduced into the inner space of the spotting tip 88 through the air hose 209 and the suction nozzle 91.

The spotting device 15 is further provided with a control circuit 213 which controls the first to third motors 204, 208 and 211, and a computer 214 which receives a detecting signal from the nozzle position sensor 212 and outputs a predetermined motor control signal to the control circuit 213 according to a predetermined sequence program.

The spotting device 15 is further provided with a temperature sensor 215 and a humidity sensor 216. Detecting signals of the sensors 215 and 216 are input into the computer 214 and the computer 214 contains therein a correcting means which corrects the discharge pressure, i.e., control of the third motor 211, according to a predetermined correction characteristic on the basis of the detecting signals of the sensors 215 and 216 in order to compensate for fluctuation in the vapor pressure.

Figure 7A:
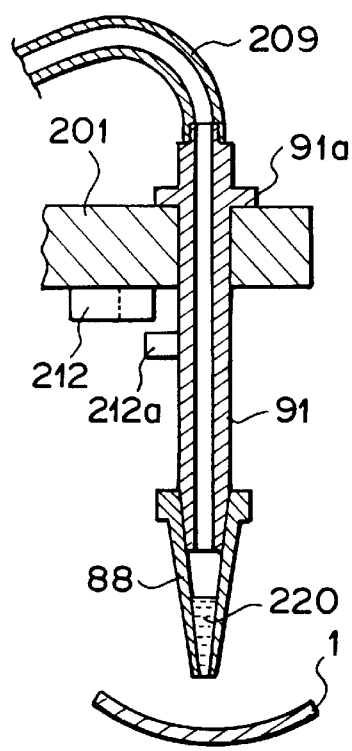
FIGS. 7A to 7C are views for illustrating an example of the procedure of spotting the sample liquid onto the frameless chemical analysis film.
Figure 7B:
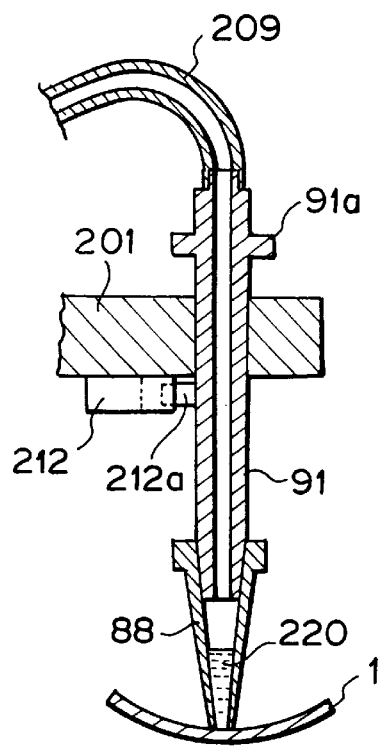
Figure 7C:
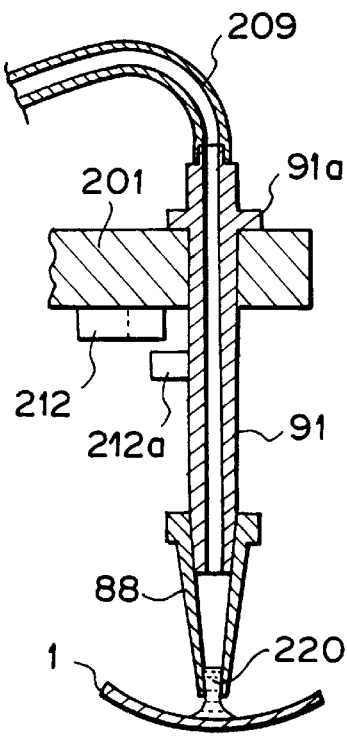

The spotting device 15 spots the sample liquid in the following manner. That is, as shown in FIG. 7A, the sample liquid 220 is sucked into the spotting tip 88 in a predetermined amount which is larger than the amount to be spotted onto the frameless chemical analysis films 1 (the amount to be spotted onto one frameless chemical analysis film x the number of the frameless chemical analysis films) and then the sampling arm 201 is swung to bring the spotting tip 88 from the initial position to the spotting position above the frameless chemical analysis film 1. Thereafter the sampling arm 201 is moved downward until the lower end of the spotting tip 88 is brought into contact with the frameless chemical analysis film 1. More specifically, the sampling arm 201 is slightly further moved downward after the lower end of the spotting tip 88 is brought into contact with the frameless chemical analysis film 1 until a flag 212a thereon is inserted into a slit of the nozzle position sensor 212 as shown in FIG. 7B. Similarly that the lower end of the spotting tip 88 is removed away from the frameless chemical analysis film 1 is detected when the flag 212a is drawn out of the slit. The position of the flag 212a relative to the position sensor 212 is so adjusted that the flag 212a is completely drawn out of the slit substantially simultaneously with a collar 91a of the nozzle 91 abutting against the upper surface of the sampling arm 201. Thereafter the vapor-pressure corrected discharge pressure is introduced into the spotting tip 88 to discharge the sample liquid 220 in a predetermined amount while the spotting tip 88 is moved upward. At this time the speed at which the spotting tip 88 is moved upward and the rate at which the sample liquid 220 is discharged are controlled according to the speed at which the sample liquid 220 spreads on the frameless chemical analysis film 1, the viscosity of the sample liquid 220 and the like so that the flow of the sample liquid 220 is not broken and the sample liquid 220 discharged on the frameless chemical analysis film 1 does not stand up to wet the side wall of the lower end portion of the spotting tip 88.

In this particular embodiment, the sample liquid 220 for a plurality of spottings is initially sucked in the spotting tip 88 and accordingly the sample liquid 220 can be immediately spotted onto another frameless chemical analysis film 1 in the same manner. In the case where the sample liquid 220 is sucked for each spotting, the sample liquid 220 is sucked over the residual sample liquid in the spotting tip 88 and then spotted onto another frameless chemical analysis film 1 in the predetermined amount in the same manner as described above.

The discharge pressure to be introduced into the spotting tip 88 is corrected so that the discharge pressure to be introduced for the first spotting becomes lower than those for the subsequent spottings.

When the sample liquid 220 is changed, that is, when the sample liquid 220 is sucked from another sample container 87, the spotting tip 88 is changed to new one. The inner space of the new spotting tip 88 is at a water vapor pressure corresponding to the environmental temperature and humidity as described above. When the sample liquid 220 is sucked in the spotting tip 88 in such a condition, the vapor pressure inside the spotting tip 88 changes with evaporation of the sample liquid 220 and rises to a saturated vapor pressure. The liquid level in the spotting tip 88 is lowered by an amount corresponding to the increase in the vapor pressure, and when the first spotting is effected with the preset discharge pressure in this state, the sample liquid 220 is discharged in an amount larger than the predetermined amount. Accordingly, the discharge pressure is corrected low by a value corresponding to the fluctuation in vapor pressure according to the temperature and the humidity at that time. In the second and the subsequent spottings, the vapor pressure inside the spotting tip 88 becomes constant since the sample liquid 220 remains in the spotting tip 88, and accordingly, the preset discharge pressure is introduced into the spotting tip 88 without correction.

The fluctuation in vapor pressure changes with the lapse of time after sample liquid 220 is sucked into a new spotting tip 88. For example the vapor pressure begins to fluctuate 2 to 3 seconds after the sample liquid 220 is sucked into the spotting tip 88 and is saturated within about 10 seconds. Accordingly, the amount of correction should be determined according to the lapse of time from sucking the sample liquid to the spotting. For example, when the first spotting is effected 10 seconds after the sample liquid 220 is sucked into the spotting tip 88, the discharge pressure for the first spotting is lowered and those for the second and the subsequent spottings need not be corrected. When a plurality of spottings are effected within 10 seconds after the sample liquid 220 is sucked into the spotting tip 88, each of the discharge pressures for the spottings effected before 10 seconds lapses should be corrected according to the fluctuation in the vapor pressure at that time.

Figure 8:
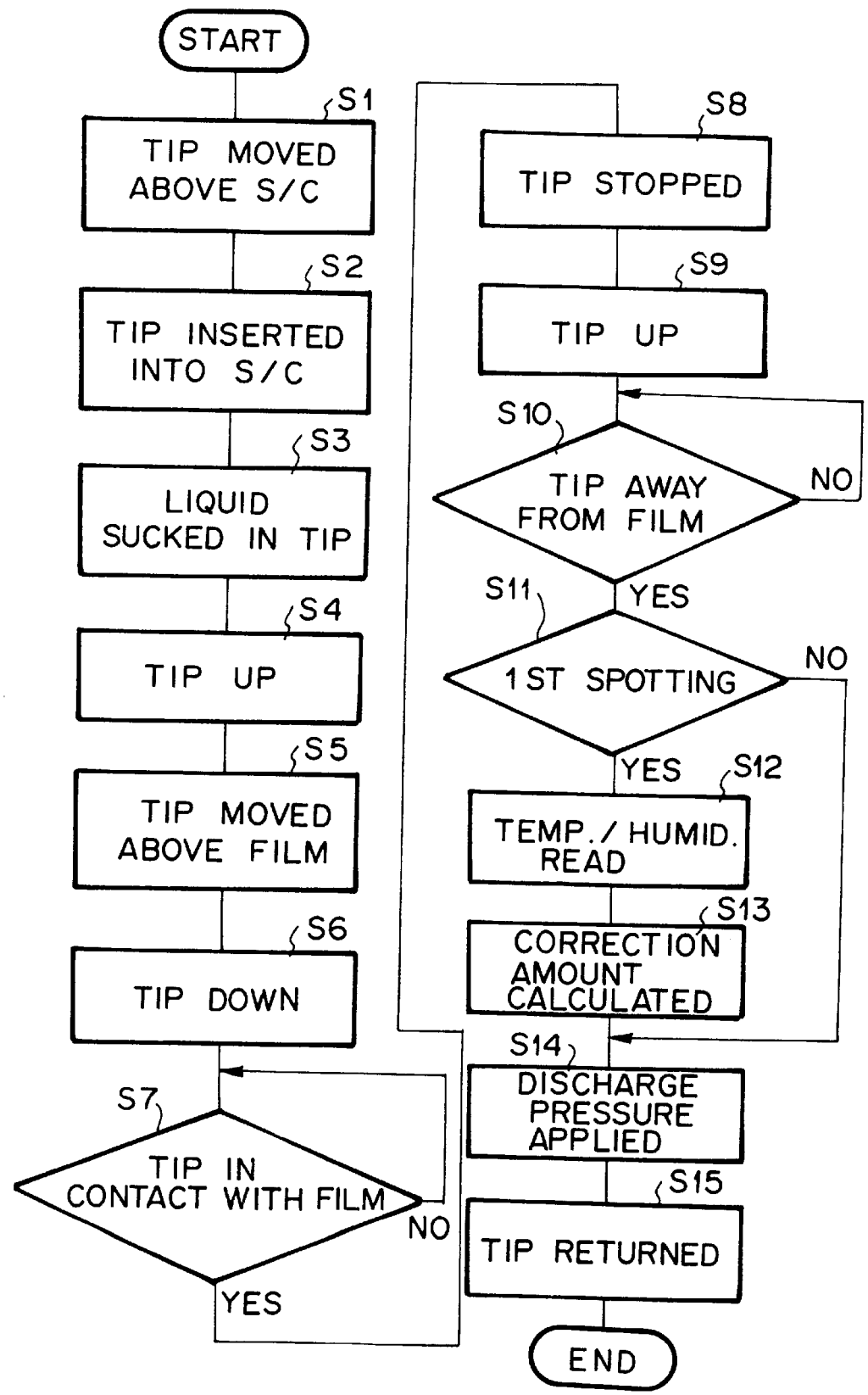
FIG. 8 is a flow chart for illustrating the spotting program executed by the computer shown in FIG. 1.

The spotting program of the computer 214 will be described with reference to FIG. 8, hereinbelow.

The computer 214 causes the control circuit 213 to output a predetermined motor drive signal to the first motor 204 to swing the sampling arm 201 (in the direction of arrow C) to bring the spotting tip 88 above the sample containers (S/C) 87. (step S1) Then the computer 214 causes the control circuit 213 to output a predetermined motor drive signal to the second motor 208 to lower the sampling arm 201 (in the direction of arrow D) to insert the lower end portion of the spotting tip 88 into the sample liquid 220 in the sample container 87. (step S2)

In this state, the computer 214 causes the control circuit 213 to output a predetermined motor drive signal to the third motor 211 to actuate the syringe 210 so that a negative pressure is generated in the air hose 209, the suction nozzle 91 and the spotting tip 88, thereby sucking the sample liquid 220 into the spotting tip 88. (step S3)

Thereafter the computer 214 causes the control circuit 213 to output a predetermined motor drive signal to the second motor 208 to move upward the sampling arm 201, thereby moving upward the spotting tip 88 (step S4), and then causes the control circuit 213 to output a predetermined motor drive signal to the first motor 204 to swing the sampling arm 201 to bring the spotting tip 88 above the frameless chemical analysis film 1 (step S5). Then the computer 214 causes the control circuit 213 to output a predetermined motor drive signal to the second motor 208 to move downward the sampling arm 201, thereby moving downward the spotting tip 88. (step S6)

When a signal representing that the lower end of the spotting tip 88 has been in contact with the frameless chemical analysis film 1 is input into the computer 214 from the nozzle position sensor 212, the computer 214 causes the control circuit 213 to output a predetermined motor drive signal to stop the second motor 208, thereby stopping the sampling arm 201. (steps S7 and S8) Then the computer 214 causes the second motor 208 to reverse to move upward the sampling arm 201. (step S9)

Figure 9:
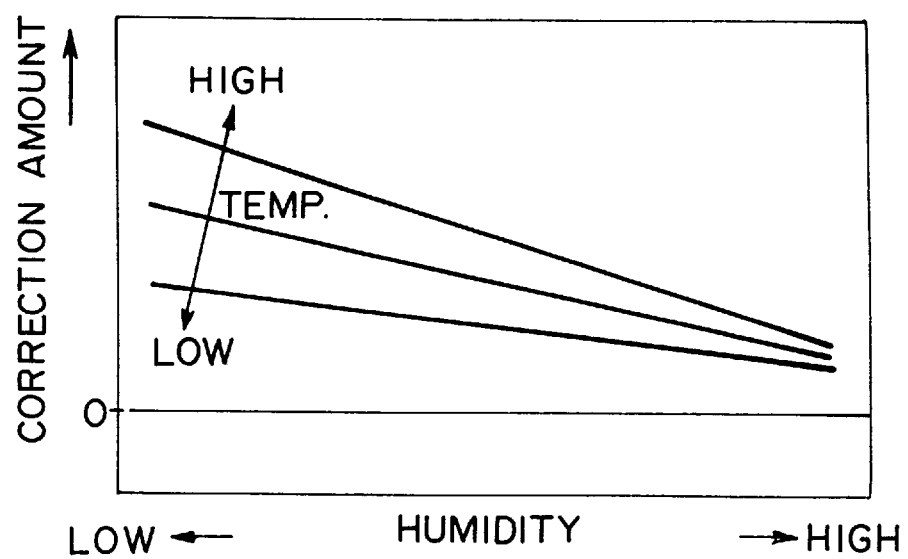
FIG. 9 is a view showing the discharge pressure correction characteristic.

When a signal representing that the lower end of the spotting tip 88 has been moved away from the frameless chemical analysis film 1 is input into the computer 214 from the nozzle position sensor 212, the computer 214 determines whether the spotting to be effected is a first one. (steps S10 and S11) When it is determined that the spotting to be effected is a first one, the computer 214 reads the signals from the temperature sensor 215 and the humidity sensor 216 (step S12), the computer 214 calculates a discharge pressure correction amount according to a correction characteristic such as shown in FIG. 9 (to be described later) on the basis of the signals from the temperature sensor 215 and the humidity sensor 216 and corrects the motor drive signal to be output from the control circuit 213 to the third motor 211 with the correction amount. (step S13) Thereafter the computer 214 executes step S14. When it is determined in step S11 that the spotting to be effected is not a first one, the computer 214 immediately executes step S14 after step S11.

In step S14, the computer 214 causes the control circuit 213 to output a motor drive signal to the third motor 211 to actuate the syringe 210 so that a predetermined discharge pressure is introduced into the air hose 209, the suction nozzle 91 and the spotting tip 88 and the sample liquid 220 in the spotting tip 88 is discharged onto the frameless chemical analysis film 1 in a predetermined amount.

Thereafter the computer 214 causes the control circuit 213 to output predetermined motor drive signals to the first and second motors 204 and 208 to return the spotting tip 88 to the initial position. (step S15)

As shown in FIG. 9, the correction amount by which the discharge pressure, i.e., the amount of rotation of the third motor 211 is reduced is increased as the temperature detected by the temperature sensor 215 increases and the humidity detected by the humidity sensor 216 decreases. The correction amounts for the various temperature and humidities are stored in a memory in the computer 214 as a correction map.

Though, in the embodiment described above, the rate at which the sampling arm 201 is moved upward and the rate (timing) at which the sample liquid 220 is discharged are controlled by detecting that the spotting tip 88 is brought into contact with the frameless chemical analysis film 1 by the sensor 212, such a sensor need not be used. That is, the sampling arm 201 is arranged to stop in the position shown in FIG. 7B and the discharge pressure is applied to the spotting tip 88 while moving upward the sampling arm 201 from the position. At the time the lower end of the spotting tip 88 begins to move away from the frameless chemical analysis film 1, the sample liquid 220 begins to be discharged from the spotting tip 88.

Figure 10A:
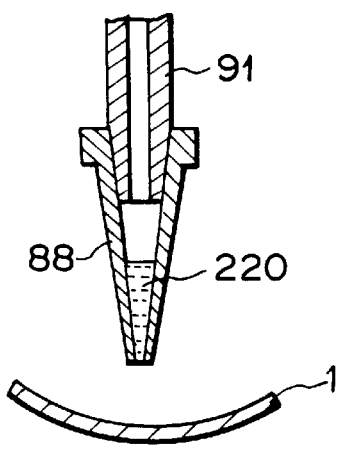
FIGS. 10A to 10E are views for illustrating another example of the procedure of spotting the sample liquid onto the frameless chemical analysis film.
Figure 10B:
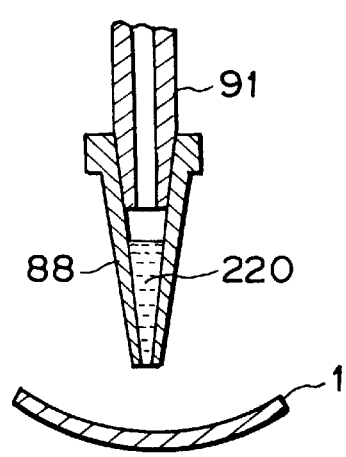
Figure 10C:
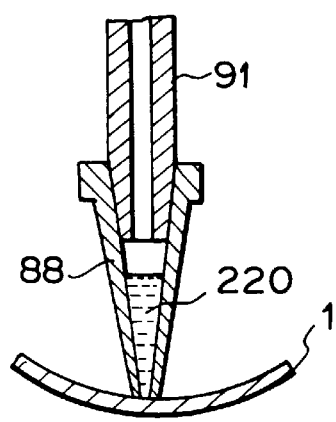
Figure 10D:
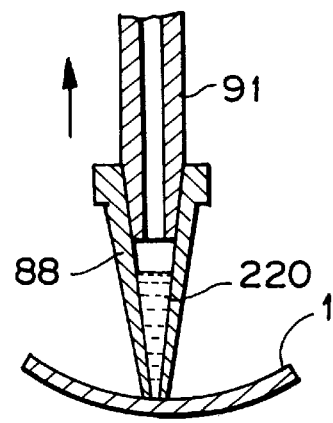

Further as shown in FIGS. 10A to 10E, after the sample liquid 220 is sucked into the spotting tip 88, a small amount of air may be sucked into the spotting tip 88 so that a small amount of air is trapped in the lower end portion of the spotting tip 88. That is, the spotting tip 88 holding therein the sample liquid 220 is first moved above the frameless chemical analysis film 1 as shown in FIG. 10A, and then the syringe 210 is actuated by the third motor 211 to generate a negative pressure in the nozzle 91, thereby sucking a small amount of air into the lower end portion of the spotting tip 88 as shown in FIG. 10B.

Figure 10E:
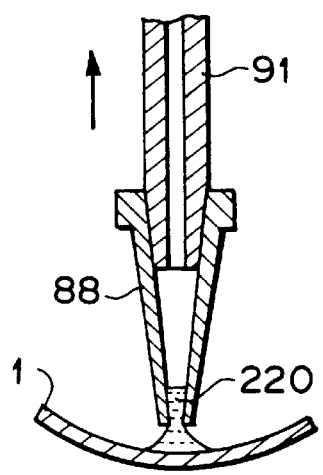
Figure 12A:
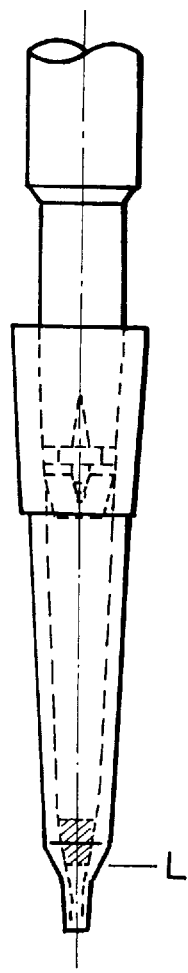
FIGS. 12A to 12C are views for illustrating the cause of fluctuation in the amount of the liquid actually spotted.
Figure 12B:
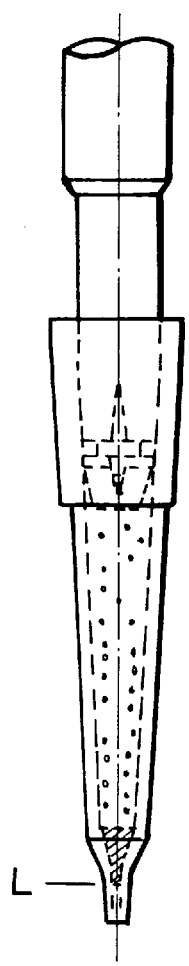
Figure 12C:
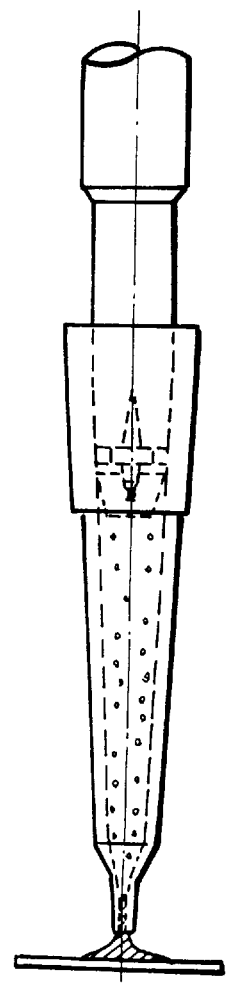
Figure 13A:
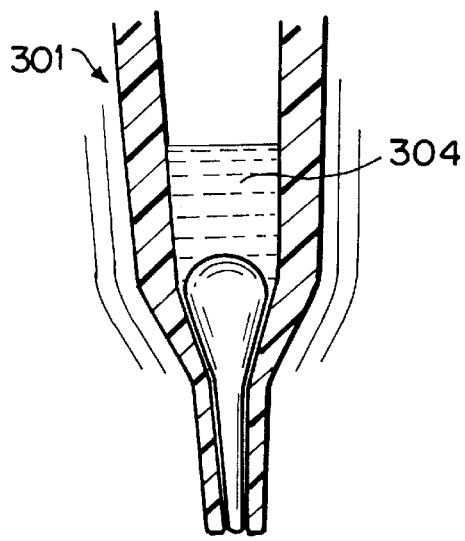
FIGS. 13A and 13B are enlarged cross-sectional views for illustrating the manner in which a bubble is formed in the liquid held in the disposable spotting tip when the liquid is sucked into the tip above the lower end thereof.
Figure 13B:
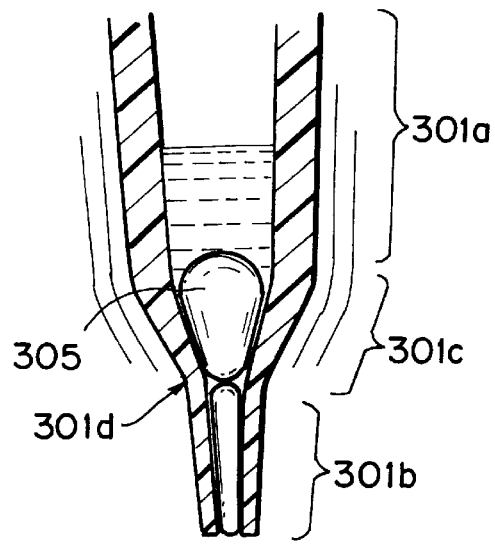

Then after once bringing the lower end of the spotting tip 88 into contact with the frameless chemical analysis film 1 (FIG. 10C), the spotting tip 88 is moved upward (FIG. 10D) while the discharge pressure begins to be applied to the suction nozzle 91 (FIG. 10E). By virtue of the air trapped in the lower end portion of the spotting tip 88, the sample liquid 220 begins to be discharged in a position where the lower end of the spotting tip 88 is at a predetermined distance from the frameless chemical analysis film 1.

The film 1 spotted with the sample liquid is transferred to the incubator 12 and incubated there. After incubation for a predetermined time, the optical density of the reagent layer 1b is measured by the light measuring system 16 (FIG. 2) disposed below the incubator 12. The light measuring system 16 comprises said light measuring head 95 for measuring the optical density of the color formed by the coloring reaction between the reagent layer 1b and the analyte in the sample liquid 220. The light measuring head 95 projects measuring light containing light of a predetermined wavelength onto the reagent layer 1b through the support sheet 1a and detects reflected light with a photodetector. Light from a light source (lamp) 96 enters the light measuring head 95 through a filter 97 and is caused to impinge upon the reagent layer 1b by the head 95. A plurality of kinds of filters 97 are mounted on a rotary disk 98 which is driven by an electric motor 99 and one of the filters 97 is selected according to the analyte.

The reflected light from the reagent layer 1b carries thereon optical information (more particularly the amount of light) on the amount of coloring substances formed by the coloring reaction between the reagent layer 1b and the sample liquid. The reflected light is received by the photodetector and the optical information carried by the reflected light is converted to an electric signal by the photodetector. The electric signal is input into a determination section through an amplifier (not shown). The determination section determines the optical density of the coloring substances formed by the coloring reaction between the reagent layer 1b and the sample liquid on the basis of the level of the electric signal and determines the concentration or the activity of a predetermined biochemical component in the sample liquid by colorimetry.

A film discharge means 17 (FIG. 2) is disposed in the film discharge position of the incubator 12. The film discharge means 17 comprises a suction pad 81 which attracts the film 1 in the cell 42 which has finished with measurement and lifts it, a horseshoe-like delivery member 82 which receives the film 1 from the suction pad 81 and transfers it outside the incubator 12 and a discarding suction pad 83 which receives the film 1 from the delivery member 82 and discards it into a discarding box 84.

The spotting tip 88 may be stopped at a predetermined distance from the frameless chemical analysis film 1 without once bringing it in contact with the film 1. Further, the member to be spotted with liquid by the liquid spotting device in accordance with the present invention need not be limited to the frameless chemical analysis film 1 but may be a chemical analysis slide, a dilution cup or the like.

A liquid spotting method in accordance with another embodiment of the present invention will be described with reference to FIGS. 14A to 14C and 15, hereinbelow. In this embodiment, the spotting tip 301 comprise an upper portion 301a having a larger diameter, a lower portion 301b having a smaller diameter and a tapered portion 301c connecting the upper and lower portions 301a and 301b.

Figure 14A:
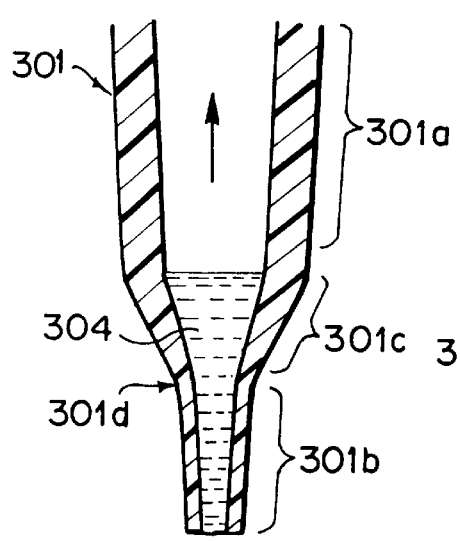
FIGS. 14A to 14C are views for illustrating movement of the liquid sucked in the spotting tip with sucking of air into the spotting tip.
Figure 14B:
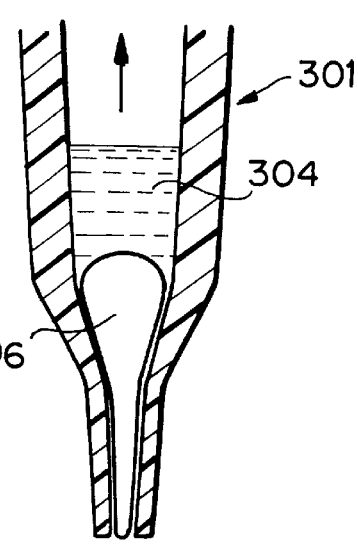
Figure 14C:
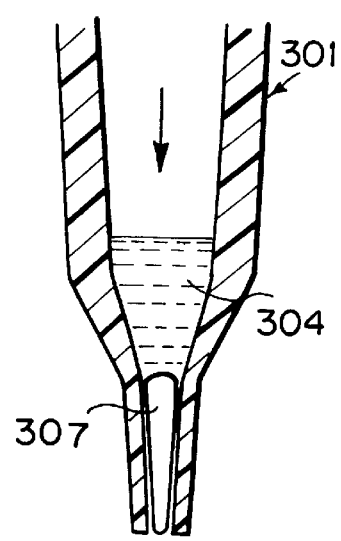
Figure 15:
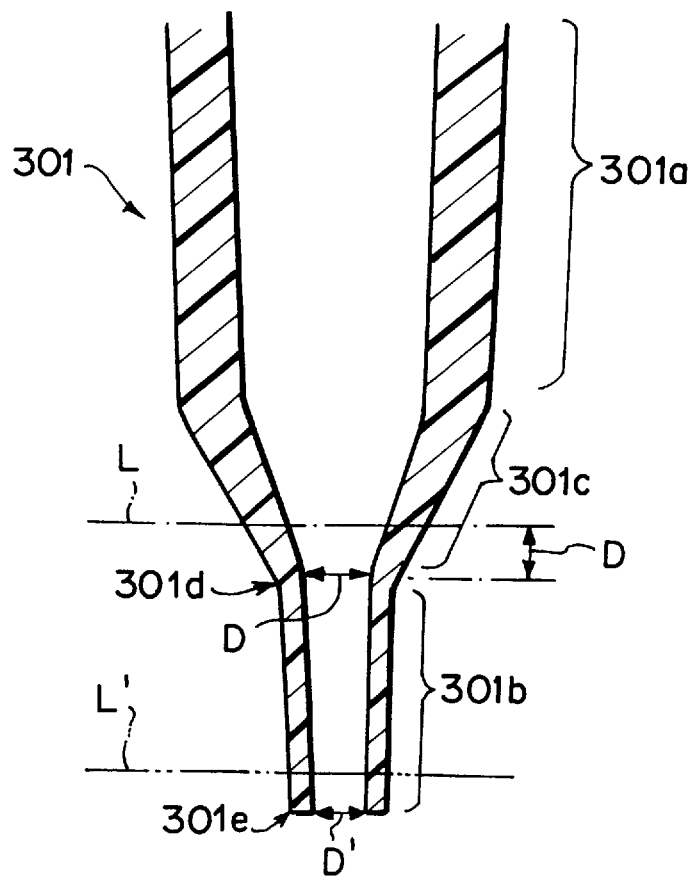
FIG. 15 is an enlarged cross-sectional view for illustrating an example of the upper and lower limits of the level of the lower surface of the liquid sucked into the spotting tip.

As shown in FIG. 14A, a predetermined amount (e.g., 13 $\mu$L) sample liquid 304 is sucked into the spotting tip 301. Thereafter a relatively large amount (e.g., 4 $\mu$L) of air 306 is once sucked into the spotting tip 301 as shown in FIG. 14B and then a part of the air 6 (e.g., 3 $\mu$L) is discharged so that 1 $\mu$L of air 307 remains in the spotting tip 301 below the lower surface of the sample liquid 304 as shown in FIG. 14C. Thus the lower surface of the sample liquid 304 in the spotting tip 301 is held near the boundary 301d between the tapered portion 301c and the lower portion 301b, that is, between an upper limit above which a bubble can be formed in the lower portion of the liquid 304 held in the spotting tip 301 when the spotting tip 301 vibrates and a lower limit below which the liquid 304 held in the spotting tip can coagulate.

For example, the upper limit may be on a level L (FIG. 15) higher than the boundary 301d between the smaller diameter portion 301b and the tapered portion 301c by the inner diameter D of the spotting tip 301 at the boundary 301d, and the lower limit may be on a level L' higher than the lower end 301e of the spotting tip 301 by the inner diameter D' of the spotting tip 301 at the lower end 301e.

What is claimed is:

1. A liquid spotting method comprising the steps of sucking liquid into a spotting tip and then sucking air into the spotting tip, wherein the improvement comprises sucking air into the spotting tip to a predetermined level where a lower surface of the liquid held in the spotting tip is positioned between an upper limit above which a bubble can be formed in a lower portion of the liquid held in the spotting tip when the spotting tip vibrates and a lower limit below which the liquid held in the spotting tip can coagulate.

2. A liquid spotting method as defined in claim 1 in which said lower limit is a position where a center of the lower surface of the liquid held in the spotting tip is on a level higher than a lower end of the spotting tip by a distance equal to an inner diameter of the spotting tip at the lower end.

3. A liquid spotting method comprising the steps of sucking liquid into a spotting tip and then sucking air into the spotting tip, the spotting tip having an upper portion of a larger diameter, a lower portion of a smaller diameter and a tapered portion connecting the upper portion and the lower portion, wherein the improvement comprises sucking air into the spotting tip to a predetermined level where a lower surface of the liquid held in the spotting tip is positioned adjacent to a boundary between the tapered portion and the lower portion of the spotting tip below an upper limit above which a bubble can be formed in a lower portion of the liquid held in the spotting tip when the spotting tip vibrates.

4. A liquid spotting method as defined in claim 3 in which said upper limit is a position where a center of the lower surface of the liquid held in the spotting tip is on a level higher than a boundary between the lower portion and the tapered portion by a distance equal to an inner diameter of the spotting tip at the boundary.

5. A liquid spotting method as defined in claim 3 in which an inner diameter of the spotting tip at the boundary between the tapered portion and the lower portion is not smaller than 0.5 mm and not larger than 2 mm.

6. A liquid spotting method comprising the steps of sucking liquid into a spotting tip and then sucking air into the spotting tip, the spotting tip having an upper portion of a larger diameter, a lower portion of a smaller diameter and a tapered portion connecting the upper portion and the lower portion, wherein the improvement comprises sucking air into the spotting tip to a predetermined level where a lower surface of the liquid held in the spotting tip is positioned between an upper limit above which a bubble can be formed in a lower portion of the liquid held in the spotting tip when the spotting tip vibrates and a lower limit below which the liquid held in the spotting tip can coagulate.

7. A liquid spotting method as defined in claim 6 in which said upper limit is a position where a center of the lower surface of the liquid held in the spotting tip is on a level higher than a boundary between the lower portion and the tapered portion by a distance equal to an inner diameter of the spotting tip at the boundary.

8. A liquid spotting method as defined in claim 6 in which said lower limit is a position where a center of the lower surface of the liquid held in the spotting tip is on a level higher than a lower end of the spotting tip by a distance equal to an inner diameter of the spotting tip at the lower end.

9. A liquid spotting method as defined in claim 6 in which an inner diameter of the spotting tip at a boundary between the lower portion and the tapered portion is not smaller than 0.5 mm and not larger than 2 mm.

\* \* \* \* \*